(12) United States Patent
Kang et al.

(10) Patent No.: US 9,888,855 B2
(45) Date of Patent: *Feb. 13, 2018

(54) REFLECTION DETECTION TYPE MEASUREMENT APPARATUS AND METHOD FOR SKIN AUTOFLUORESCENCE

(71) Applicant: Korea Electrotechnology Research Institute, Changwon (KR)

(72) Inventors: Uk Kang, Seoul (KR); Garry V. Papayan, St. Petersburg (RU)

(73) Assignee: KOREA ELECTROTECHNOLOGY RESEARCH INSTITUTE, Changwon-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 14/675,753

(22) Filed: Apr. 1, 2015

(65) Prior Publication Data

US 2015/0201839 A1    Jul. 23, 2015

Related U.S. Application Data

(63) Continuation-in-part of application No. 13/845,792, filed on Mar. 18, 2013, now Pat. No. 9,155,473.

(51) Int. Cl.
*A61B 6/00* (2006.01)
*A61B 5/00* (2006.01)

(52) U.S. Cl.
CPC ............ *A61B 5/0071* (2013.01); *A61B 5/441* (2013.01)

(58) Field of Classification Search
CPC .............................. A61B 5/0071; A61B 5/441
USPC ................................................... 600/473–480
See application file for complete search history.

(56) References Cited

U.S. PATENT DOCUMENTS

| | | | |
|---|---|---|---|
| 5,553,616 A * | 9/1996 | Ham | A61B 5/14558 128/925 |
| 5,701,902 A | 12/1997 | Vari et al. | |
| 5,784,162 A * | 7/1998 | Cabib | C12Q 1/6841 250/461.2 |
| 6,205,354 B1 * | 3/2001 | Gellermann | G01N 21/65 356/301 |
| 6,998,247 B2 * | 2/2006 | Monfre | A61B 5/14532 435/14 |
| 8,385,615 B2 * | 2/2013 | Levenson | A61B 5/0059 250/336.1 |

(Continued)

FOREIGN PATENT DOCUMENTS

| CN | 1572250 A | 2/2005 |
|---|---|---|
| CN | 100998499 A | 7/2007 |

*Primary Examiner* — Sanjay Cattungal
(74) *Attorney, Agent, or Firm* — Patent Office of Dr. Chung Park

(57) ABSTRACT

Provided is a reflection detection type measurement method for skin fluorescence. The method includes: irradiating excitation light on a measurement target; detecting a reflected light and a skin fluorescence generated from the measurement target due to the excitation light; irradiating light with a wavelength range of the skin fluorescence on the measurement target; detecting a reflected light generated from the measurement target due to the light with a wavelength range of the skin fluorescence; and calculating a skin fluorescence value of the measurement target by correcting a calculation based on the detected reflected light and skin fluorescence.

17 Claims, 10 Drawing Sheets

(56) References Cited

U.S. PATENT DOCUMENTS

| | | | |
|---|---|---|---|
| 8,634,607 B2* | 1/2014 | Levenson | A61B 5/0059 382/128 |
| 2002/0016534 A1* | 2/2002 | Trepagnier | A61B 5/0059 600/316 |
| 2002/0082487 A1* | 6/2002 | Kollias | A61B 5/0071 600/316 |
| 2002/0091324 A1* | 7/2002 | Kollias | A61B 5/0071 600/476 |
| 2004/0186363 A1 | 9/2004 | Smit | |
| 2005/0131304 A1* | 6/2005 | Stamatas | A61B 5/0071 600/476 |
| 2006/0092315 A1* | 5/2006 | Payonk | A61B 5/0071 348/370 |
| 2007/0265532 A1* | 11/2007 | Maynard | A61B 5/0071 600/477 |
| 2007/0276199 A1* | 11/2007 | Ediger | A61B 5/0071 600/300 |
| 2008/0076985 A1* | 3/2008 | Matousek | A61B 5/0059 600/310 |
| 2008/0103373 A1 | 5/2008 | Matter et al. | |
| 2009/0137908 A1* | 5/2009 | Patwardhan | A61B 5/0059 600/476 |
| 2010/0168586 A1* | 7/2010 | Hillman | G02B 23/2476 600/476 |
| 2012/0268573 A1* | 10/2012 | Schonborn | A61B 1/051 348/49 |

* cited by examiner

"A" VIEW

"B" VIEW (a)

(b)

REFLECTION DETECTION TYPE MEASUREMENT APPARATUS AND METHOD FOR SKIN AUTOFLUORESCENCE

CROSS-REFERENCE TO PRIOR APPLICATIONS

This application is a continuation-in-part of U.S. patent application Ser. No. 13/845,792, filed on Mar. 18, 2013, which in turn claims under 35 U.S.C. § 119(a) the benefit of Korean Patent Application No. 10-2012-0028675 filed Mar. 21, 2012 and Korean Patent Application No. 10-2012-0074250 filed Jul. 9, 2012, and Korean Patent Application No. 10-2013-0009774 filed Jan. 29, 2013, the entire contents of which are incorporated herein by reference.

TECHNICAL FIELD

This application relates to a skin autofluorescence measuring apparatus and method for diagnosing various diseases such as diabetes, by measuring autofluorescence of the skin from Advanced Glycation End-products (AGEs) accumulated in the skin.

BACKGROUND

Recently, various apparatuses using light for the purpose of diagnosis and treatment of diseases are being developed. Particularly, various apparatuses for diagnosing diseases using skin autofluorescence emitting out of the skin by excitation light irradiated from a light source are being developed and used.

The autofluorescence is the emission of light from the skin after excitation light is absorbed into the skin. Since having the biometric data inside the skin, the autofluorescence serves as a biomarker of diseases, and enables checking of the damage of physiological state of all body organs by a non-invasive method.

For example, Advanced Glycation End-products (AGEs) are formed via glycoxidation of proteins in human body as a result of Maillard reaction which impairs the functioning of many proteins. In general, exposure to cardiac risk factors such as smoking, intake of high fatty acid containing foods, hypercholesterolemia, and oxidative stress due to acute diseases such as sepsis lead to generation of AGEs. Thus produced AGEs are slowly decomposed and accumulated over a long period of time in the body. An increase in AGEs production is associated with the progress of chronic diseases such as atherosclerosis. With the aging process, AGEs tend to accumulate in the body throughout a person's life.

During the continuation of hyperglycemia, continual reactions of non-enzymatic protein glycation and glycoxidation occur, and thus AGEs, i.e., a complex of irreversible glycogen and protein, are formed. Accumulation of AGEs rapidly progresses in patients suffering from diabetes, renal failure and cardiovascular diseases. AGEs are accumulated in various tissues including skin. AGEs have the characteristics of irradiating autofluorescence (AF) at a range of blue spectrum (peak near about 440 nm) by excitation light irradiation of the UV range (peak near about 370 nm)

AGEs can be used as a bio marker regarding a series of diseases, and enable to evaluate physiological damages of the whole body organs by measuring autofluorescence of skin using a non-invasive method. That is, AGEs can predict long-term complications in age-related diseases. In particular, the quantity of skin autofluorescence increases in patients suffering from diabetes and renal failure, and relates to the progress of vascular complications and Coronary Heart Disease (CHD). The AGE accumulation can be measured by skin autofluorescence by a non-invasive method, a non-invasive clinical tool useful for the risk evaluation of long-term vascular complications under environments associated with the accumulation of AGEs and diabetes.

US Patent Application Publication No. 2004-186363 (hereinafter, referred to as Reference 1) discloses technology of evaluating AGEs by measuring skin fluorescence near the forearm of a patient as a method and apparatus that are proposed for AGE evaluation using skin autofluorescence measurement.

In Reference 1, an excitation light source is a blacklight fluorescent tube that emits light in a UV wavelength range of about 300 nm to about 420 nm. The collection and recording of light are performed by an optical fiber spectrometer. In order to increase a measurement area, the end surface of an optical fiber is disposed apart from a transparent window of the apparatus by a certain distance (d is about 5 mm to about 9 mm). In order to reduce an influence of light reflected from skin, the optical fiber is disposed oblique to the surface of the window at about 45 degrees.

Specifically, in Reference 1, the end surface of the optical fiber for collecting light is disposed as distant as possible from a target spot. In this case, the area of the target spot to be measured is about 0.4 cm2.

However, there is a limitation in the above method that a fluorescent signal that is collected is considerably reduced as the measurement distance (d) increases to increase the measurement area of the target spot. Accordingly, in Reference 1 according to a related art, the reliability of data detection may be reduced due to a limitation of the size of the skin area that can be measured. Particularly, such an accuracy limitation is considerably represented in parts such as moles, vessels, and wounds that are heterogeneous spots of skin.

Meanwhile, US Patent Application Publication No. 2008-103373 (hereinafter, referred to as Reference 2) discloses an apparatus for measuring AGEs to perform a screen test of a diabetic. Similarly to Reference 1, the apparatus disclosed in Reference 2 includes an optical fiber spectrometer to perform fluorescence measurement on the forearm skin. However, unlike in Reference 1, optical fiber probes are provided in a form of bundle including multiple branches.

In the apparatus of Reference 2, UV light and blue light emitting from light-emitting diodes are irradiated on the forearm of a subject through optical fiber probes, and skin fluorescence and diffusion reflection light emitting therefrom are collected through the probes. The collected light is wavelength-dispersed in a spectrometer, and then detected by a linear array detector. Two branches (illumination fibers; channel 1 and channel 2) of the optical fiber probe serve to irradiate light on a target spot, and a third branch (collection fibers) delivers light from the target to a multi-channel spectrometer. The end surface of a tissue interface, where the branch bundles of the optical fiber probes are combined, becomes in contact with skin to be irradiated.

Light from a white light LED is emitted from one branch of the optical fiber probe for reflected light spectrum measurement, and light from an appropriate LED among LEDs emitting light of ultraviolet to a blue light spectrum range is emitted from another branch of the optical fiber probe via a switching apparatus. Various wavelengths can be selected to select optimal fluorescence excitation conditions. The reflected light spectrum measurement is used to detect autofluorescence generated due to melanin and hemoglobin and compensate for the measurement result. Respective optical fibers are disposed in the optical fiber bundle by a certain sequence. Optical fibers from three branches of the optical fiber bundle are sequentially disposed in a mosaic pattern at an interval of b=0.5 mm.

In Reference 2, since light is irradiated on the forearm of a subject through an optical fiber probe, the optical fiber probe is included as an optical-transmission medium.

However, the optical fiber probe has a limitation in delivery loss for each specific wavelength which occurs according to the medium characteristics of optical fibers. Further, additional optical design and optical system are required for incidence light generated from a light source based on a total reflection condition of optical fiber.

Additionally, since both apparatuses disclosed in References 1 and 2 include optical fibers in a light-receiving unit that receives light, there is an inherent limitation in the optical fiber probe of the light-receiving unit. Since References 1 and 2 are configured to use an optical fiber spectrometer and a linear array detector, there is a limitation in that the autofluorescence signal wavelength of AGE becomes relatively smaller in a detection area that is occupied by the linear array detector. Accordingly, a detected fluorescence signal is dispersed, and the light intensity of a wavelength to be detected by the linear array detector becomes relatively smaller. Also, due to the optical fiber probe and optical fiber spectrometer, it is difficult to minimize facilities.

On the other hand, the diagnosis apparatuses disclosed in References 1 and 2 have a limitation in that it is impossible to diagnose diseases such as a diabetic foot accompanied by diabetes.

The diabetic foot is a sort of serious complications that incur a diabetic foot ulcer and a lower leg amputation according to the progress of diabetes. It is reported that the diabetic foot occurs in about 15% of all patients with diabetes and about 40% to about 60% of all lower leg amputation patients are diabetic patients. The diabetic foot ulcer is a cause in about 80% or more of all lower leg amputation patients. About 90% or more of patients with the diabetic foot can be cured without amputation when they are appropriately treated at an early stage. The autofluorescence measurement test can be used for an early diagnosis of the diabetic foot. At an early stage of the diabetic foot, the diabetic foot usually occurs in one foot before its progress in the other foot. Accordingly, the early diagnosis of the diabetic foot using the fluorescence test can be performed by comparing and evaluating the fluorescence degree of skin of the symmetrical foot part. Therefore, for early diagnosis of diseases such as diabetic foot together with typical diabetes, there is a need for the development of an apparatus that enables a selective diagnosis on body parts to be measured.

Particularly, for implementing the selective diagnosis apparatus, the miniaturization and the mobility of the apparatus has to be first prepared. Accordingly, the efficiency of light irradiation and fluorescence detection in the apparatus is needed.

Meanwhile, although such a selective diagnosis is performed on body parts, the intensity of the fluorescence generated from the skin is affected by the light scattering and absorption occurring inside the skin as well as fluorescence substances included in the skin.

Therefore, it is very important to improve the efficiency of the light irradiation and the fluorescence detection and reduce a measurement error due to the light scattering and absorption inside the skin in order to achieve an exact diagnosis on selective diagnosis parts for more clearly discriminating between persons with diseases and persons without diseases.

The above information disclosed in this Background section is only for enhancement of understanding of the background of the invention and therefore it may contain information that does not form the prior art that is already known in this country to a person of ordinary skill in the art.

SUMMARY

An embodiment of the present invention provides a reflection detection type measurement apparatus for skin fluorescence, which can simply correct a measurement error of skin fluorescence due to light scattering and absorption generated in the skin and reflected light of irradiation light from the skin surface, in measuring skin fluorescence.

An embodiment of the present invention also provides a reflection detection type measurement apparatus for skin fluorescence, which can increase a diagnosis possibility of diseases such as diabetes by exactly evaluating diagnosis factors such as AGEs from corrected skin fluorescence values.

An embodiment of the present invention also provides a reflection detection type measurement apparatus for skin fluorescence, which can improve the optical efficiency by efficiently concentrating light from a light source on the skin tissue and minimizing the specular reflection from the surface of the skin tissue, in measuring skin fluorescence.

An embodiment of the present invention also provides a reflection detection type measurement apparatus for skin fluorescence, which can improve the optical concentration and the optical uniformity by uniformly concentrating light irradiated from a light source to a measurement target.

An embodiment of the present invention also provides a reflection detection type measurement apparatus for skin fluorescence, in which an optical system and a light source system can be simply configured to conveniently perform a diagnosis process.

In accordance with an aspect of the present invention, a reflection detection type measurement method for skin fluorescence includes: irradiating excitation light on a measurement target; detecting a reflected light and a skin fluorescence generated from the measurement target due to the excitation light; irradiating light with a wavelength range of the skin fluorescence on the measurement target; detecting a reflected light generated from the measurement target due to the light with a wavelength range of the skin fluorescence; and calculating a skin fluorescence value of the measurement target by correcting a calculation based on the detected reflected light and skin fluorescence.

A dark time is maintained for a certain time before irradiating the excitation light on the measurement target, and a dark signal value of the measurement target compensates the skin fluorescence value during the dark time.

A wavelength of the excitation light has a range of 370±20 nm.

A wavelength of the skin fluorescence has a range of 440±20 nm.

The excitation light and the skin fluorescence are irradiated on the same area of the measurement target.

The excitation light is irradiated on the measurement target for a first time, and the skin fluorescence is irradiated on the measurement target for a second time after the first time.

Detecting a reflected light and a skin fluorescence generated from the measurement target due to the excitation light comprises detecting light with a specific wavelength range of the reflected light and the skin fluorescence.

A wavelength range of the reflected light is smaller than a wavelength range of the skin fluorescence.

In accordance with another aspect of the present invention, a reflection detection type measurement method for skin fluorescence includes: detecting light with a first wavelength range and light with a second wavelength range generated from a measurement target by irradiating the light with a first wavelength range on the measurement target; detecting the light with a second wavelength range generated from the measurement target by irradiating the light with a second wavelength range on the measurement target; and calculating a skin fluorescence value of the measurement target by correcting a calculation based on the detected light with a first wavelength range and light with a second wavelength range.

A reflection detection type measurement method for skin fluorescence further includes maintaining a certain dark time before irradiating the light with a first wavelength range on the measurement target.

A reflection detection type measurement method for skin fluorescence further includes maintaining a certain dark time before irradiating the light with a second wavelength range on the measurement target.

In accordance with another aspect of the present invention, a reflection detection type measurement apparatus for skin fluorescence includes: a first light source irradiating light with a first wavelength range on a measurement target; a second light source irradiating light with a second wavelength range on the measurement target; a first optical detector detecting the light with a first wavelength range generated from the measurement target by the light of the first light source; a second optical detector detecting the light with a first wavelength range generated from the measurement target by the light of the first light source, and detecting the light with a second wavelength range generated from the measurement target by the light of the second light source; and a light source switching controller controlling a turned on/off of the first light source and the second light source.

The light with a second wavelength range is longer than the light with a first wavelength range.

The light source switching controller turns off the first light source and the second light source so as to maintain a dark time for a certain time before irradiating the light of the first light source.

The light source switching controller turns off the first light source and the second light source so as to maintain a dark time for a certain time before irradiating the light of the second light source.

The first optical detector is turned off while the second optical detector detects the light generated from the measurement target due to the light with a second wavelength range.

The first optical detector and the second optical detector are turned on during a dark time maintained for a certain time before irradiating the light of the first light source.

The first optical detector and the second optical detector are turned on during a dark time maintained for a certain time before irradiating the light of the second light source.

The first wavelength range has a range of 370±20 nm.

The second wavelength range has a range of 440±20 nm.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
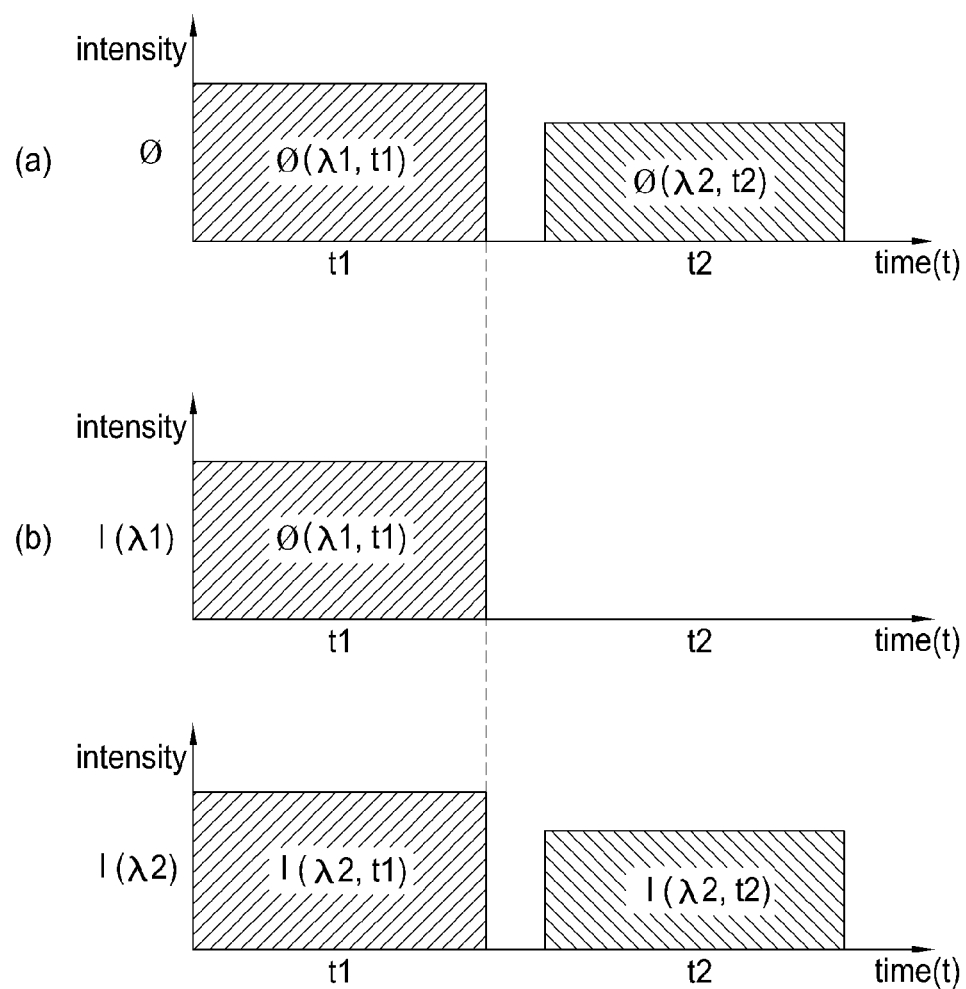
FIG. 1 is a graph illustrating the intensities of light inputted from a light source and light detected by an optical detector which are shown according to time to explain the measurement principle of a reflection detection type measurement apparatus for skin fluorescence according to an embodiment of the present invention.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The above and other features of the invention are discussed infra.

According to an embodiment of the present invention relates to a skin fluorescence measurement apparatus for irradiating excitation light on the skin and measuring skin fluorescence generated by the excitation light for the purpose of diagnosis of diseases such as diabetes. Particularly, it provides a reflection detection type measurement apparatus for skin fluorescence, which can exactly measure skin fluorescence detected at a location where reflected light is projected among skin fluorescence scattered and emitted from inside of the skin due to light irradiated on the skin.

For this, a sequential measurement may be performed on a target to be diagnosed and a reference sample, and information obtained from the target may be compared with information obtained by the reference sample to remove an individual deviation that the target has, while a light source and an optical detector may be sequentially turned on/off according to certain conditions required in the above process. Thus, provided is a reflection detection type measurement apparatus for skin fluorescence that can provide a corrected skin fluorescence value.

Hereinafter, exemplary embodiments of a reflection detection type measurement apparatus for skin fluorescence will be described in detail with reference to the accompanying drawings.

It is necessary to select a skin target for measurement of fluorescence generated on the skin and consider factors that affect the measured fluorescence. The measured fluorescence may depend on light scattering and absorption occurring inside the skin even when specular reflection occurring on the skin surface is removed, as well as fluorescent substances included in the skin. Particularly, it is necessary to correct measured fluorescence values in consideration of influences of light absorption and scattering in the fluorescence wavelength generated in fluorescent substances and the excitation light wavelength irradiated to excite fluorescent substances.

Accordingly, the following empirical Equation (1) may be considered to reduce the influence of optical factors on the fluorescent intensity.

$$AF_{corr} = AF/(R_1^{k1} R_2^{k2}) \quad (1)$$

Here, a corrected fluorescence value $AF_{corr}$ may be obtained by dividing a measured fluorescence value AF by an excitation diffusion reflection light R1 and a diffusion reflection light R2 of emission in the fluorescent wavelength range. The two diffusion reflection light values may be adjusted by exponents k1 and k2 without a degree.

Equation (1) may be used to obtain the corrected skin fluorescence value, and concrete values may be introduced to obtain the corrected skin fluorescence value through an actual test.

$I(\lambda 2, t1)$ Inherent fluorescence (skin fluorescence) signal value of skin tissue $I(\lambda 1, t1)$: Reflected light signal value of skin tissue in excitation light wavelength $I(\lambda 2, t2)$: Reflected light signal value of skin tissue in emission light wavelength k1, k2: Exponents of correction function with respect to excitation light and emission light wavelength The corrected skin fluorescence value that is newly induced may be expressed as Equation (2).

$$AF_{tissue} = [I(\lambda 2, t1)]/[I(\lambda 1, t1)^{k1} I(\lambda 2, t2)^{k2}]; k1, k2 < 1 \quad (2)$$

where $AF_{tissue}$ is a correction signal of an inherent fluorescence of a skin tissue.

The light measurement may be periodically performed at different time intervals t1 and t2. The measurement results may be averaged to increase the accuracy. The measured values may be recorded in a form of time diagram to trace the variation at an appropriate time.

Meanwhile, correction of deviations depending on equipment and correction measurement for a comparison between the results obtained from different samples may be needed. Accordingly, in the present invention, the equal measurement may be performed by introducing reference samples together with the measurement of the target skin tissue. In order to increase the measurement accuracy, the fluorescence intensity $I0(\lambda 2, t1)$ and the reflected light signal values $I0(\lambda 1, t1)$ and $I0(\lambda 2, t2)$ in the excitation light and the emission light may be similar to the optical characteristics of the skin.

The signal values generated in the measurement process of the introduced reference sample may be expressed as follows similarly to those for the target skin tissue.

$I0(\lambda 2, t1)$: Inherent fluorescence signal value of reference sample.

$I0(\lambda 1, t1)$: Reflected light signal value of reference sample in excitation light wavelength.

$I0(\lambda 2, t2)$: Reflected light signal value of reference sample in emission light wavelength.

The signals obtained from the reference samples may be processed by Equation (3) similarly to Equation (2).

$$AF_{reference} = [I_0(\lambda 2, t1)]/[I_0(\lambda 1, t1)^{k1} I_0(\lambda 2, t2)^{k2}] \quad (3)$$

A result obtained by dividing $AF_{tissue}$ by $AF_{reference}$ may be normalized, and a finally corrected inherent fluorescence value may be expressed as Equation (4).

$$AF_{corr} = K(AF_{tissue}/AF_{reference}) \quad (4)$$

$$AF_{corr} = K[I(\lambda 2, t1)/I_0(\lambda 2, t1)]/\{[I(\lambda 1, t1)/I_0(\lambda 1, t1)]^{k1} [I(\lambda 2, t2)/I_0(\lambda 2, t2)]\}^{k2} \quad (5)$$

where K is a ratio coefficient that considers the features of the used reference samples.

Equation (5) may be simplified as Equation (6)

$$AF_{corr} = K[I(\lambda 2, t1)/I_0(\lambda 2, t1)]/\{[R(\lambda 1)]^{k1} [R(\lambda 2)]\}^{k2} \quad (6)$$

$R(\lambda 1) = I(\lambda 1, t1)/I0(\lambda 1, t1)$: Diffuse reflection coefficient in excitation wavelength.

$R(\lambda 2) = I(\lambda 2, t2)/I0(\lambda 2, t2)$: Diffuse reflection coefficient in emission wavelength.

Thus, regarding the reflection detection type measurement apparatus of skin fluorescence according to the embodiment of the present invention, the corrected skin fluorescence values may be calculated by the above operation processes.

In this regard, the principle proposed for the measurement will be described in detail with reference to FIG. 1.

Figure 2:
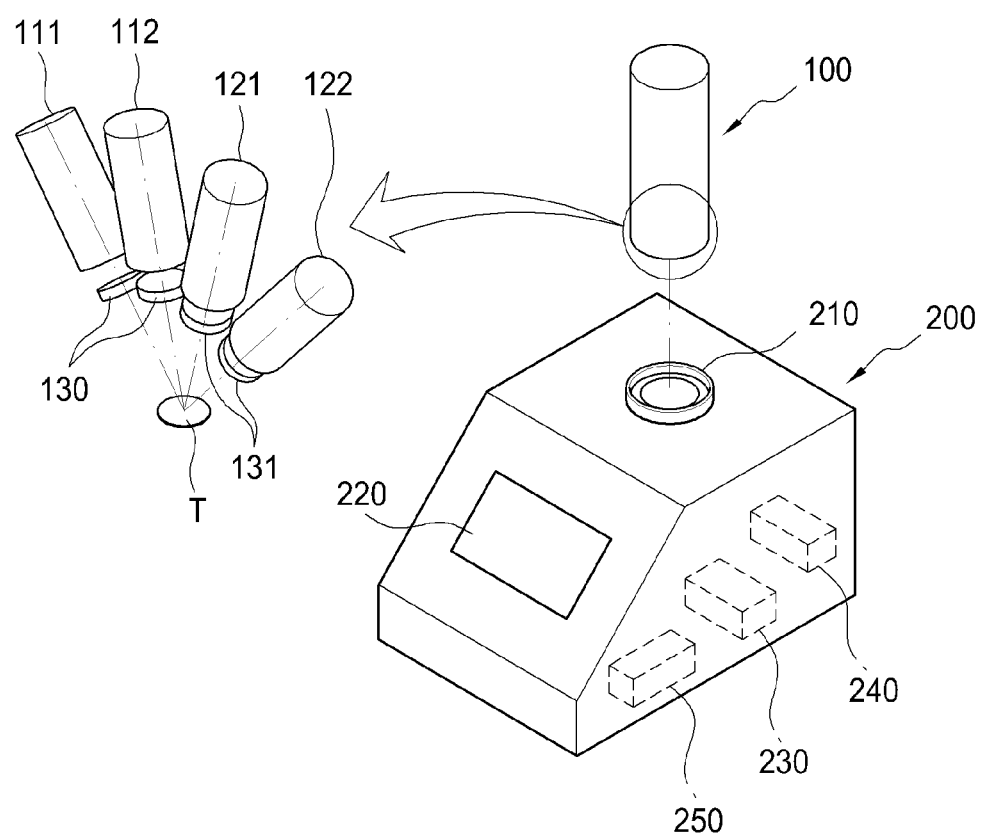
FIG. 2 is a view illustrating a reflection detection type measurement apparatus for skin fluorescence according to an embodiment of the present invention.

FIG. 1 is a graph illustrating the intensities of light inputted from a light source and light detected by an optical detector which are shown according to time to explain the measurement principle of a reflection detection type measurement apparatus for skin fluorescence according to an embodiment of the present invention, and FIG. 2 is a view illustrating a reflection detection type measurement apparatus for skin fluorescence according to an embodiment of the present invention. Based on FIG. 1 and FIG. 2, first, as shown in FIG. 1, in the reflection detection type measurement apparatus for skin fluorescence, the measurement may be successively performed under a first condition in which light corresponding to a wavelength range (first wavelength λ1) of excitation light is irradiated as an input, and a second condition in which light corresponding to a wavelength range (second wavelength λ2) of skin fluorescence generated by the excitation light is irradiated while being separated from each other in time.

The wavelength range of the irradiation light corresponding to the first and second conditions may be selectively configured according to the skin fluorescence to be detected. For example, considering that the skin fluorescence is detected with respect to AGE in an exemplary embodiment, light with the first wave length of 370 nm±20 nm may be used as the excitation light for the fluorescence excitation under the first condition, and light with the second wave length of 440 nm±20 nm corresponding to the wavelength of the skin fluorescence with respect to AGE may be selectively used under the second condition.

That is, as shown in FIG. 2, the measurement may be performed using a measurement scanner 100 including light sources 111 and 112 for emitting two different wavelengths of light and an optical detector 121, 122 for detecting two different wavelengths of light. The measurement may be performed by contacting the measurement scanner 100 with the skin tissue corresponding to a measurement target in the diagnosis observance process or the reference sample in the correction process.

In regard to the measurement process, FIG. 1A shows an operating time diagram showing the respective light sources with respect to two different wavelengths operate while being separated from each other in time. In this case, light $\varphi(\lambda1, t1)$ irradiated from a first light source 111 that is an excitation light source may be configured to exist in a different and uncrossed time from light $\varphi(\lambda2, t2)$ irradiated from a second light source 112 that is a reference light source of different wavelength range.

Meanwhile, FIG. 1B shows an operating time diagram with respect to two optical detectors. In the same time while light $\varphi(\lambda1,t1)$ is being radiated from the first light source 111, two signals may be generated with respect to the excited skin fluorescence and the reflected light. Two signals generated in the excitation light wavelength may be a reflected light signal $I(\lambda1,t1)$ and an excited fluorescence signal $I(\lambda2,t1)$.

Meanwhile, only a single signal may be generated in a time when light $\varphi(\lambda2,t2)$ is irradiated from the second light source 112. The signal generated by the second light source 112 may be only a reflected light signal $I(\lambda2,t2)$ in the wavelength range of the irradiated light.

As shown in FIG. 1, in the reflection detection type measurement apparatus for skin fluorescence according to an embodiment of the present invention, the light irradiation of the first light source 111 and the light irradiation of the second light source 112 may be sequentially performed on the measurement target T while being separated from each other in time. In this case, the signals detected from the optical detector may be collected upon each light irradiation, and then may be calculated using the above equations to output the corrected skin fluorescence value.

FIG. 2 is a view illustrating a reflection detection type measurement apparatus for skin fluorescence according to an embodiment of the present invention, which is implemented by the measurement principle described above.

As shown in FIG. 2, the reflection detection type measurement apparatus for skin fluorescence according to an embodiment of the present invention may include a measurement scanner 100 that irradiates excitation light on the skin and detects skin fluorescence, and a main body 200 that is connected to the measurement scanner 100 and analyzes data detected by the measurement scanner 100 to display the data.

However, it will be only an exemplary configuration that the measurement scanner 100 and the main body 200 are configured to be separated from each other. Accordingly, if necessary, the reflection detection type measurement apparatus for skin fluorescence may be manufactured in a form of a single sensor without a separate main body, or may further include other components connected thereto.

The reflection detection type measurement apparatus for skin fluorescence according to an embodiment of the present invention may be configured to include a light source 111, 112 and an optical detector 121, 122 to irradiate light on a target to be measured and detect skin fluorescence generated by the irradiated light.

In an embodiment of the present invention, in order to provide exact skin fluorescence values by correcting the detected skin fluorescence values, the reflection detection type measurement apparatus for skin fluorescence may include two light sources that irradiate different wavelengths of light and two optical detectors that can detect different wavelengths of reflected light and skin fluorescence generated by the two irradiation lights.

Specifically, the two light sources may include the first light source 111 that emits light corresponding to the wavelength range (first wavelength λ1) of the excitation light and the second light source 112 that emits light corresponding to the wavelength range (second wavelength λ2) of skin fluorescence generated by a target inside of a measurement object due to the excitation light. The two optical detectors may include a first optical detector 121 for detecting reflected light λ1 reflected from the measurement object by the excitation light emitted from the first light source 111 and a second optical detector 122 for detecting the skin fluorescence λ2 emitted from the target inside of the measurement object due to the excitation light and the reflected light λ2 reflected from the measurement object by the reflected light from the second light source 112.

Therefore, the two light sources and optical detectors may be configured to simultaneously detect the reflected light and the skin fluorescence. For example, the two light sources and optical detectors may be disposed at one end of the measurement scanner 100, and may be close to each other so as to irradiate light on the measurement target T and detect the reflected light.

In this case, light may be irradiated on the same area of the first light source 111 and the second light source 112, and the first optical detector 121 and the second optical detector 122 may be disposed to detect light generated from the same area of the measurement target. If light is irradiated on an area other than the same area of the measurement object, it is difficult to obtain an accurate result value when calculation for measuring the skin fluorescence is corrected. In addition, it is preferable that the same area of the measurement object is set as a local area. If the same area of the measurement object is set as a broad area, it is difficult to expect accurate result value because it is actually obtained through a complicated process when calculation is corrected based on the light detection in a corresponding area, and an additional component for complicated calculation is required and cost is increased.

In addition, the first optical detector 121 and the second optical detector 122 may difficult to detect an actually necessary light signal value due to a generated noise when the excitation light or the skin fluorescence generated from the measurement object is totally reflected from the measurement object, and an error of necessary light signal value may be generated due to noise. Accordingly, the first optical detector 121 should be disposed in an area except for the total reflection area to which the excitation light of the first light source is reflected after irradiating to the measurement target. In addition, it is preferable that the second optical detector 122 is also disposed in an area except for the total reflection area to which the excitation light of the first light source and the light of the second light source are reflected after irradiating to the measurement target.

In an exemplary embodiment of the present invention, in order to detect the skin fluorescence with respect to AGE, light with the first wavelength of 370 nm±20 nm may be used as excitation light for fluorescence excitation, and light with the second wavelength of 440 nm±20 nm corresponding to the wavelength of the skin fluorescence with respect to AGE may be used as the reflected light.

That is, it is preferable that light of a wavelength range of skin fluorescence generated from the measurement target by the excitation light of the first light source may be used as the light of the second light source.

In this case, the first light source 111 may include a light emitting diode that irradiates light of the first wavelength range, 370 nm±20 nm. The second light source 112 may include a light emitting diode that irradiates light of the second wavelength range, 440 nm±20 nm. In addition, the first optical detector 121 may include a photodiode that detects light of the first wavelength range, and the second optical detector 122 may include a photodiode that detects light of the second wavelength range.

In an exemplary embodiment of the present invention, it was described that the first light source 111 and the second light source 112 have wavelength ranges of 370 nm±20 nm and 440 nm±20 nm. However, the light source may have a wavelength range corresponding to the target when reaction conditions are different depending on the target to be measured inside of the skin.

Meanwhile, the reflection detection type measurement apparatus for skin fluorescence according to an embodiment of the present invention may further include a light source switching control unit 230 for controlling turning on/off of the first and second light sources 111 and 112. More preferably, the reflection detection type measurement apparatus for skin fluorescence may further include an optical detector switching control unit 240 for controlling turning on/off of the first and second optical detectors 121 and 122.

The light source switching control unit 230 and the optical detector switching control unit 240 may control switching such that the light sources and the optical detectors can exactly operate according to the detection conditions of the skin fluorescence and the reflected light in order to exactly calculate the skin fluorescence values.

The light source switching control unit 230 may be configured to turn on or off the light sources according to the light irradiation conditions of the reflection detection type measurement apparatus for skin fluorescence. For example, under the first condition in which excitation light $\lambda 1$ is irradiated on the measurement target, the second light source 112 may be turned off and the first light source 111 may be turned on, controlling switching of the light sources such that only the first light source 111 irradiates light of a first wavelength range. On the other hand, under the second condition in which the reflected light $\lambda 2$ of a different wavelength range from the excitation light is irradiated on the measurement target, the first light source 111 may be turned off and the second light source 112 may be turned on such that light of a second wavelength range is irradiated from only the second ling source 112.

That is, the light source switching control unit 230 may control switching of the first light source 111 and the second light source 112 such that the first light source 111 and the second light source 112 are turned on in a different time.

Similarly, the optical detector switching control unit 240 may be configured to control turning on/off of the optical detectors according to the measurement conditions. The optical detector switching control unit may be configured to power on/off the optical detectors for detecting light of a wavelength range to be detected under a current measurement condition.

Particularly, since an optical signal with respect to the second wavelength may need to be detected under both first condition in which the excitation light of the first wavelength range is irradiated and second condition in which the reflected light of the second wavelength range is irradiated, the second optical detector 122 for detecting light with respect to the second wavelength may be maintained turned on.

That is, the first optical detectors 121 may be turned on so that reflected light for the light irradiated from the first light source 111 for a first time may be detected, and the second optical detector 122 may be turned on so that reflected light for the light irradiated from the second light source 112 for a second time after the first time and the skin fluorescence due to the light irradiated from the first light source 111 for the first time may be detected.

In this case, the switching control may be sequentially performed on the light sources for a certain time during the whole measurement process including the first condition and the second condition. In regard to the period of switching with respect to each light source, the switching control may be performed at a high frequency of about 10 Hz to about 10 kHz such that the variation of the diffusion reflectance due to the blood flow does not affect the measurement by considering the pulse rate of the human body.

As the measurement scanner 100 of the reflection detection type measurement apparatus for skin fluorescence is manufactured in a hand-grippable form, such high-speed switching may achieve measurement on the substantially same target spot even when the measurement scanner 100 is moved by a scanning method in which the skin fluorescence is continuously measured while the scanner is moving.

Although not shown in FIG. 2, the reflection detection type measurement apparatus for skin fluorescence may include an optical filter selectively disposed at the front of the light source and the optical detector. Preferably, in order to prevent the detection of the skin fluorescence with a relatively lower light intensity from becoming difficult due to specular reflection of irradiated light on the skin surface, a pair of polarizers 130 and a pair of cross-polarizers 131 may be disposed between corresponding light sources and optical detectors.

The polarizers and the cross-polarizers may need to be disposed at mutually-crossing locations on a pair of the first light source 111 and the first optical detector 121 and a pair of the second light source 112 and the second optical detector 122, respectively.

Meanwhile, the reflection detection type measurement apparatus for skin fluorescence may be configured to include the main body 200 that is configured to be connectable to the measurement scanner 100 including two light sources and two optical detectors. The main body 200 may be configured to include an operation part 250 that calculates the value of corrected skin fluorescence from data measured by the measurement scanner 100.

The main body 200 may be configured to be optically, electrically and mechanically connectable to the measurement scanner 100.

Specifically, the main body 200 may include a mounting part 210 with a shape matching the shape of a measurement terminal of the measurement scanner 100 such that the measurement scanner 100 can be mechanically mounted onto the main body 200. The measurement scanner 100 may be fixedly mounted into the mounting part 210 through mechanical coupling.

In an exemplary embodiment of the present invention, the first and second light sources 111 and 112 and the first and second optical detectors 121 and 122 may be configured to be disposed in the measurement scanner 100, while the mounting part 210 may be configured to have an aperture formed in a shape corresponding to the shape of one end portion of the measurement scanner 100, allowing the light sources and the optical detectors to be fixed in the mounting part 210 while facing each other.

As the measurement scanner 100 is mounted onto the main body 200, the main body 200 may be configured to be electrically connectable to the measurement scanner 100, allowing the measurement scanner 100 to irradiate light on the measurement target T and acquire data about the detected skin fluorescence and the reflected light. In addition, a reference sample for comparison with the measurement target T may be disposed on the mounting part 210 of the main body 200, and the light sources and the optical detectors of the measurement scanner 100 may be configured to be optically connected to the reference sample when the measurement scanner 100 is seated on the mounting part 210 of the main body. In this case, the reference sample may be selected so as to have the optical characteristics of the diffuse reflection and fluorescence similar to the human body's tissue that is measured.

Therefore, when the measurement scanner 100 is mounted onto the mounting part 210 of the main body 200 to be electrically and optically connected, the measurement scanner 100 may perform light irradiation and light detection processes, which have been performed on the measurement target T, on the reference sample. The measured data of the measurement target and the reference sample may be transmitted to the operation part 250 of the main body 200.

The operation part 250 may calculate corrected skin fluorescence values regarding the actual measurement target using data about the fluorescence signals and the reflected light signals that are received. The calculation result may be displayed via the display part 220 on the main body 200.

The above sequential measurement may be repeated. In order to perform an operation process in which correction is performed according to the results of the repeated measurement, all measured data may be stored in the measurement scanner 100 via a memory. Preferably, the measurement results may be stored in a form of time diagram to trace the variation of the measurement results.

A charging terminal (not shown) may be disposed in the mounting part 210 on the main body 200 to charge the measurement scanner 100. The charging terminal may be configured to perform charging when the measurement scanner 100 is mechanically coupled to the mounting part 210.

If necessary, the measurement scanner 100 may be configured to be connected to the main body 200 through Bluetooth.

Figure 3:
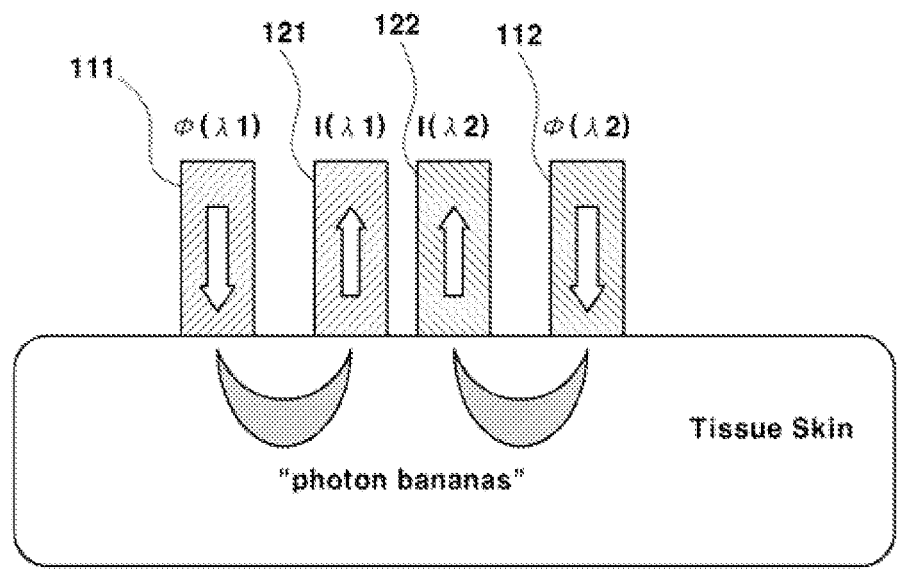
FIG. 3 is a view illustrating an exemplary arrangement of light sources and optical detectors when there is no gap between the light sources and the optical detectors and a target skin in a reflection detection type measurement apparatus for skin fluorescence according to an embodiment of the present invention.
Figure 4:
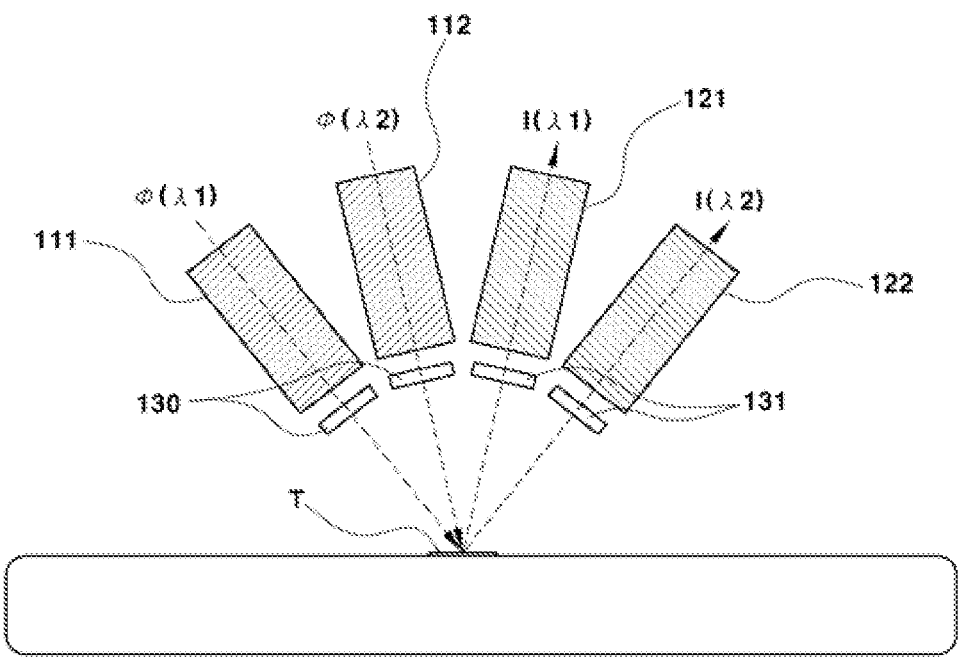
FIG. 4 is a view illustrating an exemplary arrangement of light sources and optical detectors when there is a gap between the light sources and the optical detectors and a target skin in a reflection detection type measurement apparatus for skin fluorescence according to an embodiment of the present invention.

An exemplary arrangement of the light sources and the optical detectors in the reflection detection type measurement apparatus for skin fluorescence is shown in FIGS. 3 and 4.

FIG. 3 is a view illustrating an exemplary arrangement of light sources and optical detectors when there is no gap between the light sources/optical detectors and the measurement target. FIG. 4 is a view illustrating an exemplary arrangement of light sources and optical detectors when there is a gap between the light sources/optical detectors and the measurement target.

As shown in FIG. 3, the light sources and the optical detectors may be disposed parallel to each other and perpendicular to the measurement target, respectively. In order to form an optimum detection region, the first light source 111 and the second light source 112 may be disposed at the outer sides, respectively, and the first optical detector 121 and the second optical detector 122 may be disposed between the first and second light sources 111 and 112.

As shown in FIG. 4, when a certain gap exists between the light sources/optical detectors and the measurement target, the light sources and the optical detectors may be obliquely disposed to be inclined with respect to each other, and may be configured to form light irradiation paths and light detection paths such that the light sources can irradiate light on the same region of the measurement target and the optical detectors can detect light generated in the same region, respectively. Preferably, the light source and the optical detector corresponding to each other may be disposed to be inclined at an angle of about 45 degrees with respect to each other. For example, when a light source vertically irradiates light on the skin surface, an optical detector may be disposed to be inclined at an angle of about 45 degrees with respect to the light source, thereby reducing an influence of specular reflection. An angle between the first and second light sources 111 and 112 and the first and second optical detectors 121 and 122 may be minimized according to the structure of equipment. More preferably, the influence of the specular reflection may be minimized by disposing a pair of polarizers 130 and a pair of cross-polarizers 131 between corresponding light source and optical detector at the front of the light sources and the optical detectors together with optical filters to remove the specular reflected light.

In this case, the first light source 111, the second light source 112, the first optical detector 121, and the second optical detector 122 may be configured to be connected to the end of the measurement target side of the measurement scanner 100 via a light guide, respectively. A transparent protection film such as a glass plate may be disposed on the contact surface between the skin and the sensor to protect the measurement scanner 100 from foreign substances such as external moisture.

Hereinafter, a test example of the light irradiation, the light detection, and the operation process performed by the reflection detection type measurement apparatus for skin fluorescence configured as above will be described as follows.

Example 1

It is necessary to perform measurement on a measurement target and a reference sample, two targets that are introduced to obtain a corrected fluorescence value. Light measurement is performed on the human body's skin that is the measurement target among the two targets.

For diagnosis, the measurement is performed by a light source and an optical detector that contact or get close to the measurement target on the upper arm of a subject. A measurement scanner moves along the skin surface to scan the target part of about 5 cm2 to about 19 cm2.

Before the measurement, all light sources are turned off, and then level evaluation of a dark signal is performed to automatically compensate for light leaking from the outside. That is, a dark time may be maintained for a certain time with respect to the measurement target and a dark signal of the measurement target may be used to compensate the value of skin fluorescence for a dark time.

A light module sequentially operates light $\varphi(\lambda 1, t1)$ of first light source with a wavelength $\lambda 1$ and light $\varphi(\lambda 2, t2)$ of second light source with a wavelength $\lambda 2$ at different time intervals t1 and t2, respectively.

During the whole measurement process, light generated by two light sources is sequentially radiated at time intervals t1 and t2 while switching on/off is being repeated at a period of about 50 Hz.

Next, light irradiated from the light sources is detected by the optical detectors to be converted into electrical signals.

The light $\varphi(\lambda 1, t1)$ of the first light source of a near-ultraviolet spectrum range (near 370 nm) excites the fluorescence of a target to form a corresponding signal $I(\lambda 2, t1)$ by the optical detector, and forms a signal $I(\lambda 1, t1)$ proportional to excitation reflected light diffuse-reflected by the skin that is the measurement target.

The light $\varphi(\lambda 2, t2)$ of the second light source of a blue spectrum range (near 440 nm) corresponds to the maximum value of the inherent fluorescence generated in AGE and NADH, and forms a signal $I(\lambda 2, t2)$ proportional to the reflected light that is diffuse-reflected by the target skin.

The above measurement is repeatedly and periodically performed at different time intervals t1 and t2, and the measurement results are averaged and stored.

The same measurement processes are performed on the reference sample, and data calculated in each process is processed in an operation part to calculate a corrected skin fluorescence value.

A time diagram regarding the actuation of the light sources having two wavelengths in the above test example may be shown as Table 1 below.

TABLE 1

| | 1st Cycle | | | | 2nd Cycle | | | |
|---|---|---|---|---|---|---|---|---|
| | Dark | F440/R365 | Dark | R440 | Dark | F440/R365 | Dark | R440 | Dark |
| LED365 | OFF | ON | OFF | OFF | OFF | ON | OFF | OFF | OFF |
| LED440 | OFF | OFF | OFF | ON | OFF | OFF | OFF | ON | OFF |
| PD365 | ON | ON | ON | OFF | ON | ON | ON | OFF | ON |
| PD440 | ON | ON | ON | ON | ON | ON | ON | ON | ON |

In Table 1, the first light source and the second light source correspond to LED 365, LED 440 respectively, and the first optical detector and the second optical detector correspond to PD 365, PD 440 respectively As shown in Table 1, in the skin fluorescence measurement of the measurement target, a dark time may be maintained for a certain time before the light source is turned on at a first step. In this case, the first optical detector and the second optical detector may maintain a turned-on state. At a second step, the first light source is turned on. In this case, in a state in which the second optical detector is maintained to be turned off, the first optical detector and the second optical detector may be turned off so as to detect light generated by the first light source. Thereafter, at a third step, a dark time may be maintained before the second light source is turned on, and the first optical detector and the second optical detector may be still maintained to be turned off. Finally, at a fourth step, the second light source may be turned on. In this case, in a state in which the first light source is maintained to be turned off, the first optical detector is turned off and the second optical detector is maintained to be turned on. As described above, throughout the first step to the fourth step, the skin fluorescence value may be measured from the measurement target, and may be repeatedly performed with a cycle including the first step to the fourth step.

In this test example, the respective cycle time is configured to be about 20 ms. Also, the measurement target scanning time is calculated as about 2 seconds, and 100 measurement cycles are performed.

Data measured in this test example is stored and preserved in an internal memory of the measurement scanner. When the measurement scanner is placed on the mounting part of the main body, the detection information is automatically moved to the operation part of the main body to undergo an operation according to function conversion and be statistically processed, and the measurement results are displayed.

Meanwhile, the present invention proposes a structure in which an optical prism and an optical connector are disposed on an optical path such that the optical transmission and detection efficiencies can be improved.

Figure 5:
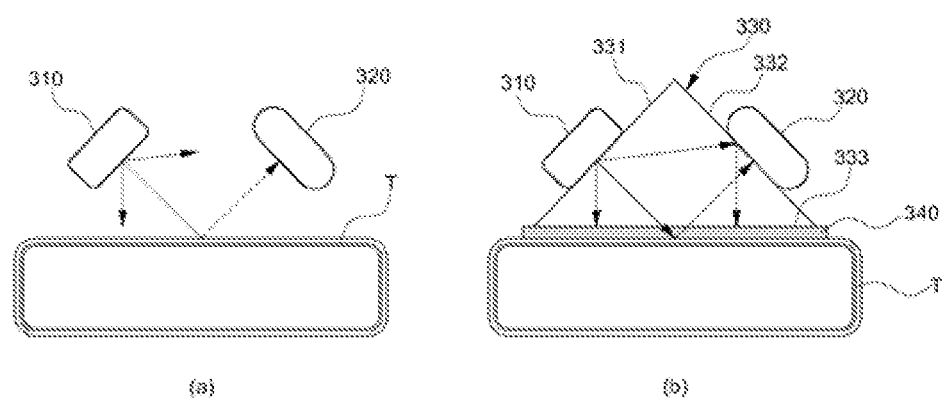
FIG. 5 is a view illustrating an optical prism and an optical connector in a reflection detection type measurement apparatus for skin fluorescence according to an embodiment of the present invention.

FIG. 5 illustrates a reflection detection type measurement apparatus for skin fluorescence according to an embodiment of the present invention, compared with a typical reflection detection type measurement apparatus for skin fluorescence. FIG. 5A illustrates the optical irradiation and the optical detection without an optical prism and an optical connection. FIG. 5B illustrates the optical irradiation and the optical detection with an optical prism and an optical connection.

In a case where the optical irradiation and the optical detection are performed without an optical prism and an optical connector as shown in FIG. 5A, excitation light may be irradiated from a light source 310, and then an optical detector 320 may detect fluorescence caused by the excitation light.

In this case, as shown in FIG. 5A, since the light source 310 such as a Light Emitting Diode (LED) used as an excitation light source irradiates light with a wide divergence angle, an optical loss may occur on a measurement target, and scattering of fluorescence from the skin on which light is irradiated may cause a loss of the quantity of light detected by the optical detector 320.

Since the skin fluorescence detected is significantly smaller than other excitation light or reflected light thereof, the optical loss may considerably reduce the accuracy of the measurement and the reliability of the diagnosis even when the optical loss is slight.

On the other hand, in order to prevent the optical loss, a reflection detection type measurement apparatus for skin fluorescence including an optical prism is proposed as shown in FIG. 5B.

Referring to FIG. 5B, the excitation light irradiated from the light source 310 may be concentrated by the optical prism 330, and the optical uniformity of a skin part that is the measurement target can be improved.

Specifically, the optical prism 330 may have two upper inclination surfaces 331 and 332 that are adjacent to the light source 310 and the optical detector 320, respectively, and a lower surface 333 that is adjacent to the skin. Excitation light irradiated from the upper inclination surface 331 adjacent to the light source 310 with a wide divergent angle may be totally reflected from the inside of the upper inclination surface 332 of the optical prism 330 at the side of the optical detector 320 may be maximally concentrated on the skin, thereby reducing the non-uniformity of the light source, i.e., the characteristics in which the optical intensity becomes smaller at the outer side of the optical axis than at the center of the optical axis and thus achieving improved optical uniformity.

Also, the optical prism 330 may serve to concentrate a secondary light generated by light transmitted to the skin tissue part on the optical detector 320. Accordingly, in the reflection detection type measurement apparatus for skin fluorescence, an optical signal can be improved, and a measurement error can be reduced. Thus, an optical measurement can be performed on a wide skin part without a scanning method of an optical sensor.

The reflection detection type measurement apparatus for skin fluorescence according to the embodiment of the present invention may be configured to include an optical connector 340 for reducing a specular reflection component reflected by the surface of the skin that is the measurement target and allowing light to effectively penetrate into the skin.

The optical connector 340 may be configured to locate between the undersurface 333 of the optical prism 330 adjacent to the skin that is the measurement target and the surface of the skin, and may contact the undersurface 333 of the optical prism and the surface of the skin, respectively.

The optical connector 340 may contact the undersurface 333 of the optical prism 330 and the surface of the skin to serve as a connection layer for allowing a smooth optical contact with an appropriate refractive index at the boundaries thereof. The optical connector 340 may prevent the specular reflection from the surface of the skin, and may allow light to effectively penetrate into the skin.

The optical connector 340 may have a certain refractive index between two media to prevent a light leakage that may occur between the two media due to the refraction and scattering of the excitation light between the optical prism 330 and the skin tissue, and may serve to fill uneven portions such as fine unevenness of the skin tissue.

The optical connector 340 may be formed of an elastic material or a liquid material such as water or oil-immersion. The optical connector 340 may be formed of a material having a refractive index similar to those of the optical prism 330 and the skin.

Due to the optical connector 340, the total internal reflection of the irradiated light may not occur at the boundaries between the prism and the skin tissue, and the penetration efficiency of light emitting from the light source into the skin can be significantly improved.

Accordingly, the reflection detection type measurement apparatus for skin fluorescence including the optical prism 330 and the optical connector 340 can improve the optical concentration and the optical uniformity, and can significantly reduce the specular reflection component of light irradiated from the light source by the surface of the skin.

Example 2

A reflection detection type measurement apparatus for skin fluorescence including an optical prism and an optical connector was manufactured. Also, as a comparative example, an apparatus configured such that a light source and an optical detector are located similarly to those of the reflection detection type measurement apparatus and optical irradiation and optical detection are performed without the optical prism and the optical connector was manufactured.

In this test example, a UV LED (No 33, Nichia) emitting light of about 365 nm was used as the light source, and an optical fiber spectrometer (AVaspec-2048) was used as the optical detector. Also, an optical photodiode may also be used as the optical detector. A commercialized model (Right Angle Prism, Uncoated, 20 mm, Edmund Optics) was used as the optical prism.

In this test example, water was used as the optical connector, which was interposed between the optical prism and the surface of the skin that is the measurement target.

A specular reflection component of light irradiated from the light source in the reflection detection type measurement apparatus of the test example was measured, and a specular reflection component in the apparatus of the comparative example was also measured.

In the measurement results from the test example and the comparative example, the specular reflection component of the test example was measured to be reduced by about ten times or more compared to that of the comparative example.

Figure 6:
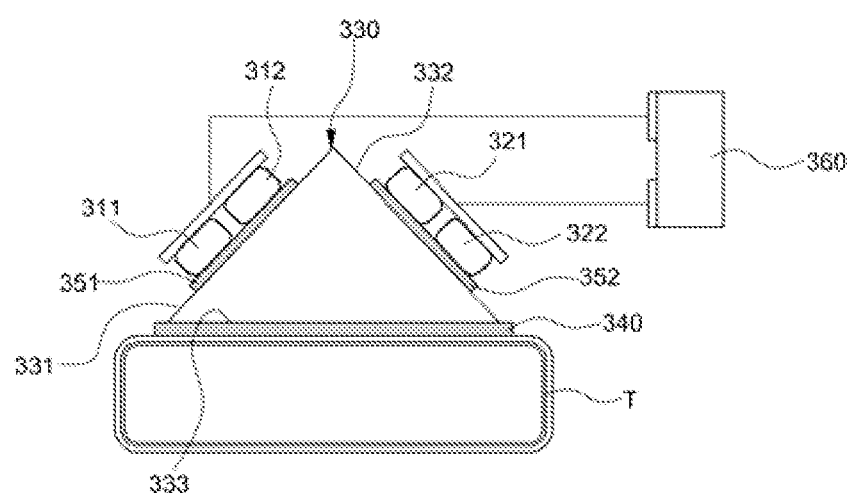
FIGS. 6 through 10 are views illustrating an optical prism and an optical connector in a reflection detection type measurement apparatus for skin fluorescence according to an embodiment of the present invention.

FIG. 6 illustrates a reflection detection type measurement apparatus for skin fluorescence including two light sources 311 and 312 and two optical detectors 321 and 322, which is configured as shown in the test examples 1 and 2. Like in FIG. 5, an optical prism 330 and an optical connector 340 may be interposed between the two light sources 311 and 312 and the two optical detectors 321 and 322 and the skin T that is the measurement target.

In this embodiment, the optical prism 330 may have two upper inclination surfaces 331 and 332 adjacent to the light source and the optical detector, respectively, and a lower surface 333 adjacent to the skin. A triangular prism 330 333 having a triangular section may be used like in FIG. 5. Preferably, the two light sources 311 and 312 may be disposed on the upper inclination surface 331 of the triangular prism 330, and the two optical detectors 321 and 322 may be disposed on the upper inclination surface 332 of the triangular prism, allowing the undersurface 333 of the prism 330 to contact the skin.

In this case, when the two different light sources 311 and 312 are disposed on the upper inclination surface 331, the optical axes of the two light sources 311 and 312 may differ from each other. Accordingly, the regions of the skin T on which the light is irradiated may differ from each other.

However, since the light source is connected to the measurement target T through the optical prism 330, uniform light in which the difference between the optical axes can be corrected by the optical reflection inside the optical prism 330 can be obtained.

Also, a polarizer 351 may be disposed between the light sources 311 and 312 and the optical prism 330, and a cross polarizer 352 may be disposed between the optical detectors 321 and 322 and the optical prism 330. As shown in FIG. 6, the polarizer 351 may be disposed on the upper inclination surface of the optical prism 330 under the first and second light sources 311 and 312, and the cross polarizer 352 may be disposed on the other upper inclination surface of the optical prism 330 under the first and second optical detectors 321 and 322.

As shown in FIG. 6, the optical connector 340 may be disposed between the skin T that is the measurement target and the undersurface 333 of the optical prism 330. The optical connector 340 may contact the undersurface 333 of the optical prism 330 and the surface of the skin T, respectively, allowing smooth optical contact with an appropriate refractive index at the boundaries thereof.

Accordingly, the specular reflection component generated from the surface of the skin T by the optical connector 340 can be reduced, and light partially reflected by a difference of the refractive index between the surface of the skin T and the optical connector 340 can be additionally inhibited by the cross polarizer 352 disposed at the front of the optical detectors 321 and 322.

The reflection detection type measurement apparatus for skin fluorescence may be configured to be connected to a main body 360 that includes a light source switching controller for controlling turning on/off of the first and second light source 311 and 312 and an operator for calculating a correction value of a skin fluorescence signal from a detected fluorescence signal and a reflected light signal.

As described in FIG. 2, in the reflection detection type measurement apparatus for skin fluorescence according to this embodiment, the light source 311 and 312 and the optical detectors 321 and 322 may also be disposed at one end of a measurement scanner, and a corrected skin fluorescence value can be obtained by an operation process similar to that of FIG. 2 except that the light irradiation is performed through the optical prism disposed between the light source and the measurement target.

Figure 7:
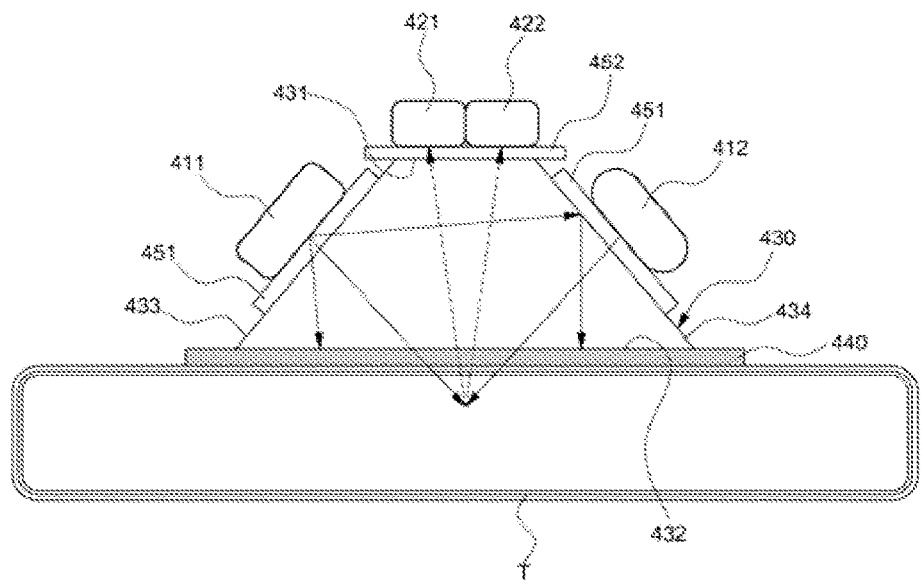

FIG. 7 illustrates a reflection detection type measurement apparatus for skin fluorescence according to another embodiment of the present invention. As shown in FIG. 7, the reflection detection type measurement apparatus may include an optical prism 430 of a trapezoidal section having an upper surface 431, a lower surface 432, and two inclination surfaces 433 and 434, and an optical connector 440 interposed between the lower surface 432 and the skin T. Two light sources 411 and 412 may be disposed over the two inclination surface 433 and 434, respectively, and two optical detectors 421 and 422 may be disposed over the upper surface 431 of the optical prism 430.

Unlike FIG. 6, the optical prism 430 may have a trapezoidal section, which further has the upper surface in addition to the two upper inclination surfaces and the undersurface.

Specifically, the optical prism 430 may be formed to have a trapezoidal shape in which the upper surface 431 is further included in addition to the two upper inclination surfaces 433 and 434 adjacent to the light source and the optical detector, respectively, and the lower surface 432 adjacent to the skin T. Also, the light sources 411 and 412 and the optical detectors 421 and 422 may be disposed over the two upper inclination surfaces 433 and 434 and the upper surface 431, respectively.

In this embodiment, the first light source 411 and the second light source 412 irradiating light having a wavelength different from the first light source 411 may be disposed over the upper inclination surfaces 433 and 434 of the optical prism 430, respectively. Also, the first and second optical detectors 421 and 422 may be disposed over the upper surface 431 connected to the two upper inclination surfaces 433 and 434 to detect light having different wavelengths regarding a fluorescence signal and a reflected light signal.

Similarly to FIG. 6, a polarizer 451 and a cross polarizer 452 may be disposed between the light source 411 and 412 or the optical detectors 421 and 422 and the optical prism 430 to remove reflected light, respectively. As shown in FIG. 7, the polarizer 451 may be disposed between the first and second light source 411 and 412 and the upper inclination surfaces 433 and 434 of the optical prism 430, and the cross polarizer 452 may be disposed between the first and second optical detector 421 and 422 and the upper inclination surface 431 of the optical prism 430.

Also, an optical connector 440 may be disposed between the undersurface 432 of the optical prism 430 and the skin T that is the measurement target. The optical connector 440 may contact the undersurface 432 of the optical prism 430 and the surface of the skin T, respectively.

Figure 8:
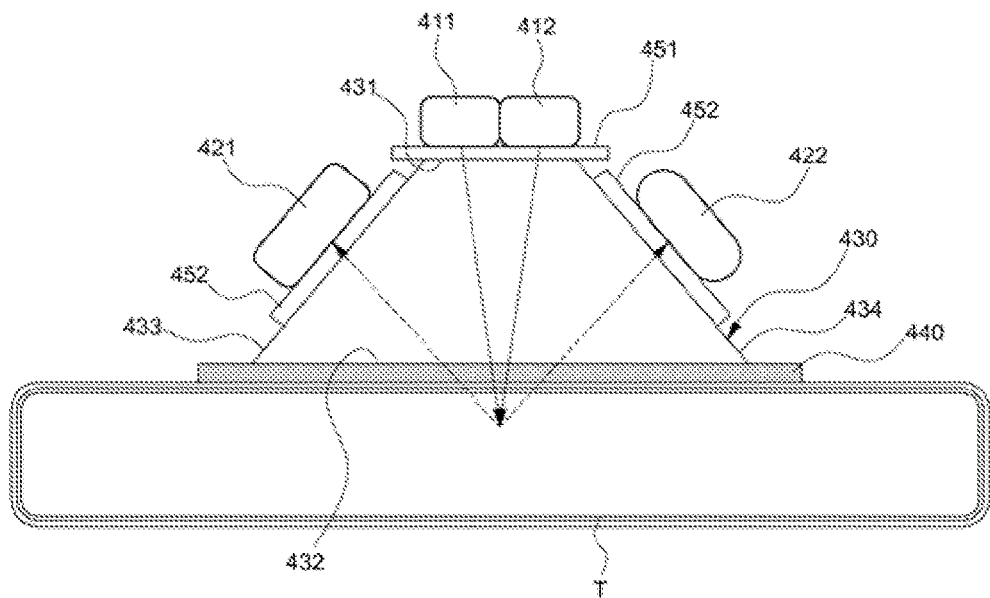
Figure 9:
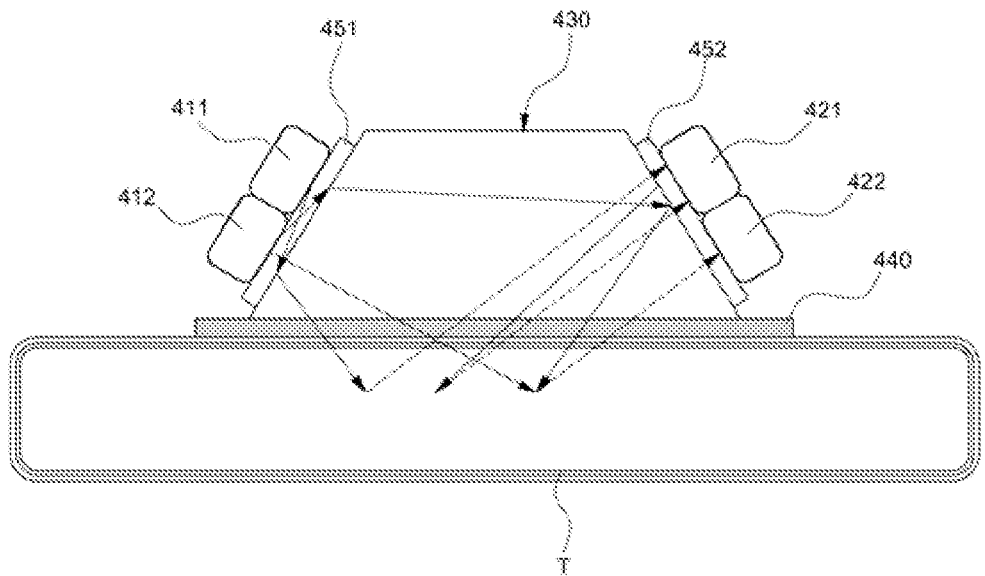

FIGS. 8 and 9 illustrate reflection detection type measurement apparatuses for skin fluorescence according to other embodiments of the present invention. In these embodiments, optical prisms having trapezoidal sections may be used similarly to that of FIG. 7, but the arrangement of light sources and optical detectors is different from each other.

In FIG. 8, two light sources 411 and 412 may be disposed over the upper surface 431 of an optical prism 430, and two optical detectors 421 and 422 may be disposed over two upper inclination surfaces 433 and 434, respectively.

In FIG. 9, two light sources 411 and 412 may be disposed over one upper inclination surface 433 of an optical prism 430, and two optical detectors 421 and 422 may be disposed over the other upper inclination surface 434 of the optical prism 430.

Figure 10:
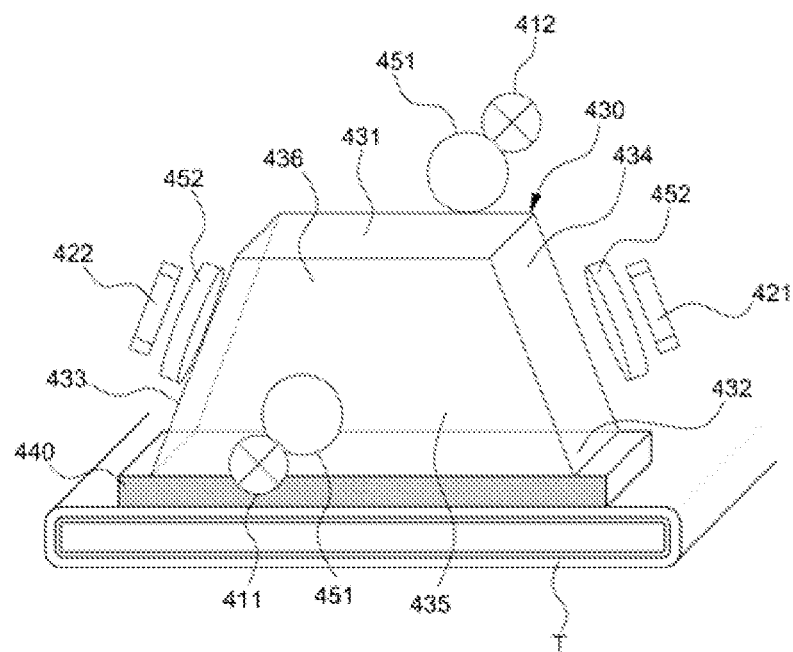

FIG. 10 illustrates a reflection detection type measurement apparatus for skin fluorescence according to another embodiment of the present invention. In this embodiment, an optical prism 430 of a trapezoidal section having four upper inclination surfaces 433, 434, 435 and 436 may be disposed. Here, two light sources 411 and 412 and two optical detectors 421 and 422 may be disposed over the upper inclination surfaces 433, 434, 435 and 436 such that the two light sources 411 and 412 and the two optical detectors 421 and 422 face each other, respectively.

As shown in FIG. 10, the first light source 411 and the second light source 412 may be selectively disposed over the two upper inclination surfaces 435 and 436, and the first optical detector 421 and the second optical detector 422 may be selectively disposed over the other two upper inclination surfaces 433 and 434.

The first and second light sources 411 and 412 may be disposed over the two upper inclination surfaces 435 and 436 that are opposite to each other, and the first optical detector 421 and the second optical detector 422 may be disposed over the two upper inclination surfaces 433 and 434 that are opposite to each other.

In this case, the light sources 411 and 412 and the optical detectors 421 and 422 may be disposed orthogonally to each other. Such the orthogonal arrangement may reduce a specular reflection component.

A reflection detection type measurement apparatus for skin fluorescence according to an embodiment of the present invention may include a holder to which the first light source 411, the second light source 412, the first optical detector 421, and the second optical detector 422 are inserted to be disposed to face the same area of the measurement target. Such the holder may have a specific shape, for a typical example, a shape of pyramid, so as to measure the light generated from the measurement target due to the light irradiated from the first and second light sources.

A reflection detection type measurement apparatus for skin fluorescence according to an embodiment of the present invention may be configured to have a structure in which two light sources 111 and 112 and two optical detectors 121 and 122 are disposed at four sides of such a holder, respectively. The measurement principle of the pyramidal measurement apparatus for skin fluorescence may be substantially similar to the case where the light source and the optical detector are disposed side by side as shown in FIG. 1.

Figure 11:
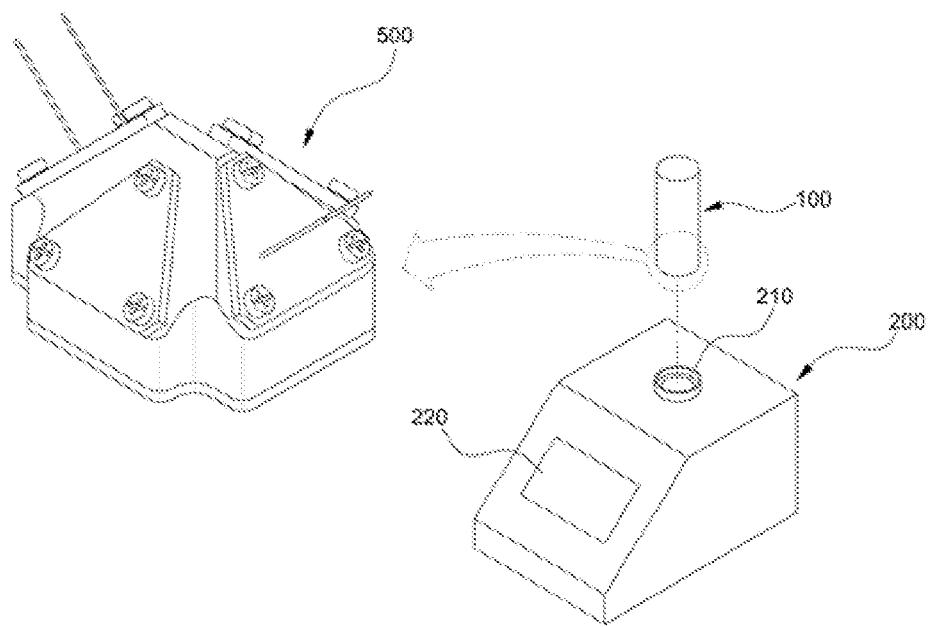
FIG. 11 is a view illustrating a reflection detection type measurement for skin fluorescence according to an embodiment of the present invention, which is configured to include a housing equipped with two light sources and two optical detectors.
Figure 12:
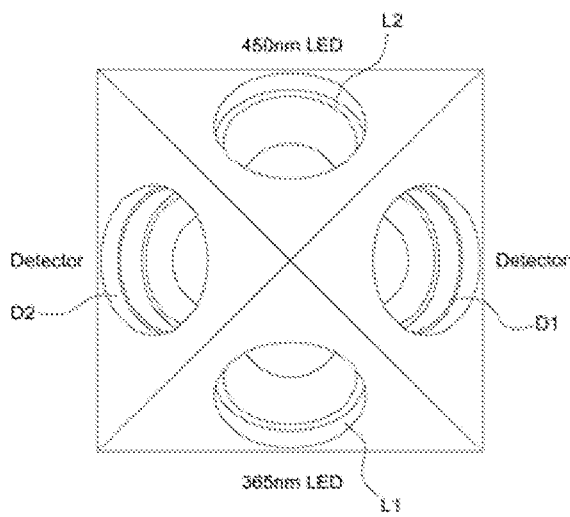
FIG. 12 is a plan view illustrating a pyramidal holder in which light sources and optical detectors are installed in a reflection detection pyramidal measurement apparatus for skin fluorescence according to an embodiment of the present invention.

In this regard, FIG. 11 illustrates a pyramidal holder equipped with two light sources and two optical detectors, and FIG. 12 is a plan view illustrating the pyramidal holder.

As shown in FIG. 11, a reflection detection type measurement apparatus for skin fluorescence according to an embodiment of the present invention may include a measurement scanner 100 that can irradiate excitation light and detect skin fluorescence and a main body 200 that is connected to the scanner 100 to analyze information detected from the scanner and display the information.

However, this configuration in which the measurement scanner 100 and the main body 200 are separately provided is merely one of exemplary embodiments of the present invention, Accordingly, a separate main body may not be provided according to a need, but may be manufactured in a single sensor type, and other components may be additionally connected thereto.

The light source and the optical detector may be disposed on a pyramidal measurement module 500 disposed on one end of the measurement scanner 100.

That is, the two light sources and the two optical detectors may be mounted in the four side surfaces of the pyramidal holder to form the pyramidal measurement module 500 disposed on one end of the measurement scanner 100 as shown in FIG. 11.

More specifically, as shown in FIG. 12, the pyramidal holder constituting the pyramidal measurement module 500 may have four through-holes in four side surfaces thereof, and the four through-holes may receive the light sources L1 and L2 and the optical detectors D1 and D2, respectively.

In this case, as shown in FIG. 12, the light sources L1 and L2 may be mounted in two side surfaces of the pyramidal holder opposite to each other with respect to different wavelengths, respectively, and the optical detectors D1 and D2 are mounted in the other two side surfaces of the pyramidal holder opposite to each other with respect to different wavelengths, respectively.

In this arrangement, when considering the irradiation angle of light and the main optical path of the reflected light according thereto, the direct inflow of reflected light to the optical detector may reduce.

Figure 13:
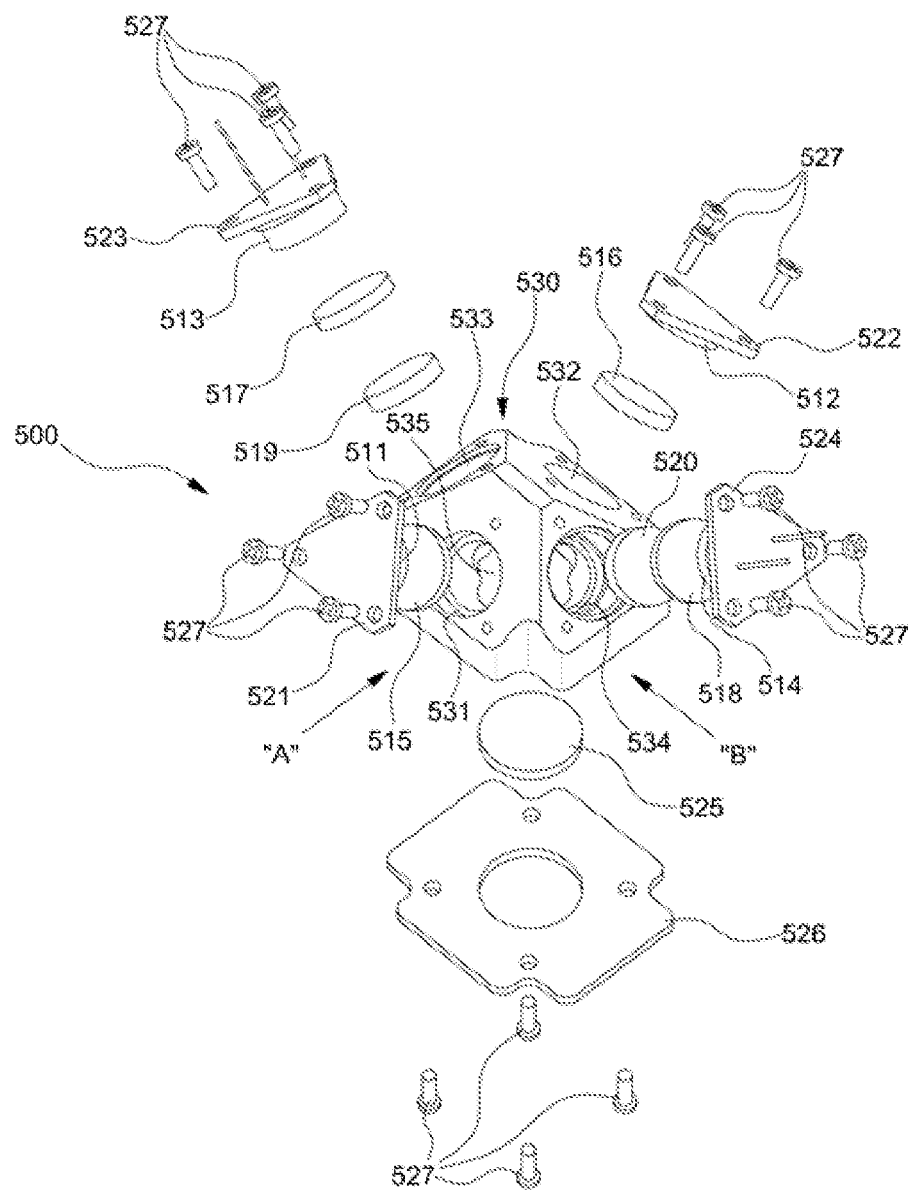
FIGS. 13 through 15 are exploded views illustrating a pyramidal measurement module of a reflection detection pyramidal measurement apparatus for skin fluorescence according to an embodiment of the present invention.
Figure 14:
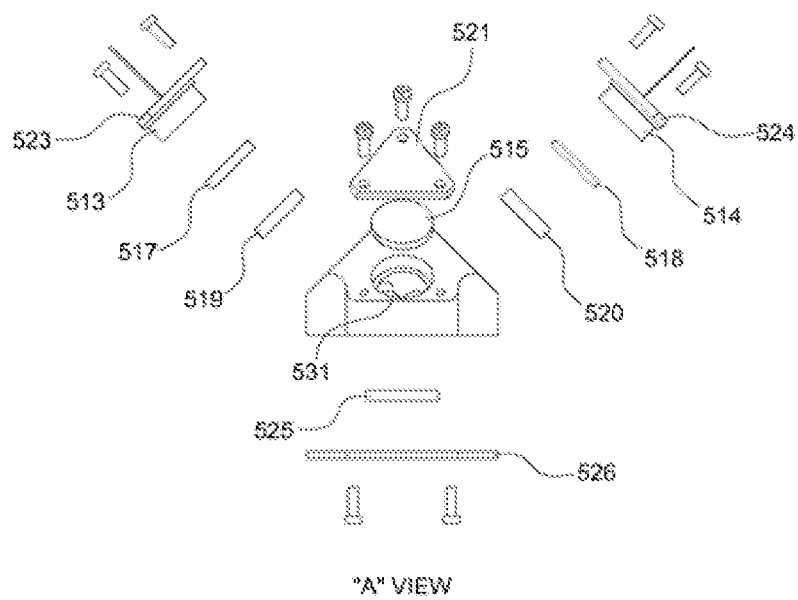
Figure 15:
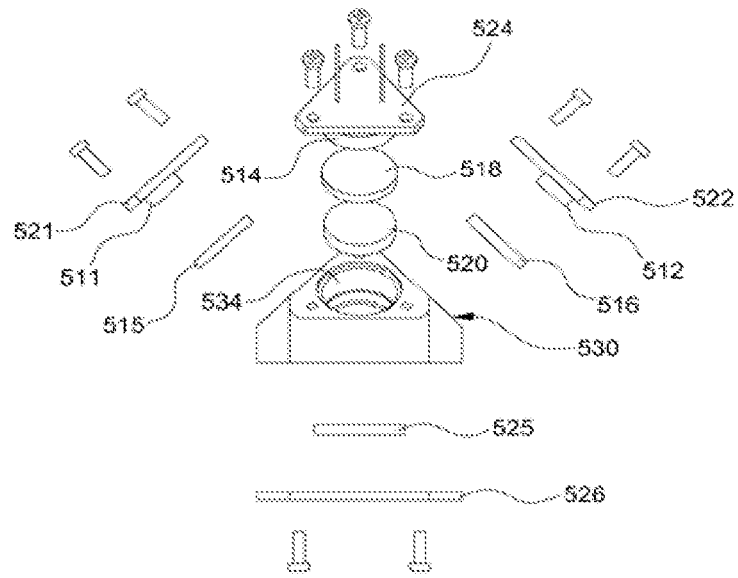

FIGS. 13 through 15 illustrate the concrete configuration of a pyramidal measurement module 500 of a reflection detection pyramidal measurement apparatus for skin fluorescence according to an embodiment of the present invention.

FIG. 13 is an exploded perspective view of a pyramidal measurement module according to an embodiment of the present invention. FIGS. 14 and 15 are side views when viewed from arrows "A" and "B" of FIG. 13.

As shown in FIG. 13, the pyramidal module 500 of the reflection detection pyramidal measurement apparatus for skin fluorescence may include two light sources and two optical detectors, and a pyramidal holder 530 equipped with the light sources and the optical detectors.

The pyramidal holder 530 may have a pyramidal shape having four side surfaces and one bottom surface. The light sources and the optical detectors may be installed in the side surfaces of the pyramidal holder 530, respectively.

More specifically, four through-holes 531, 532, 533 and 534 may be formed in the side surface of the pyramidal holder 530 to receive the light sources and the optical detectors. That is, as shown in FIG. 12, the first through-hole 531 formed in one side surface of the pyramidal hold 530 may receive the first light source 511, and the second through-hole 532 opposite thereto may receive the second light source 512. Also, the third through-hole 533 and the fourth through-hole 534 may be formed in the two side surfaces between the two side surfaces having the first through-hole 531 and the second through-hole 532, respectively. The third through-hole 533 may receive the first optical detector 513 and the fourth through-hole 534 may receive the second optical detector 514.

In this case, the two light sources may be disposed so as to obliquely irradiate light from the side surfaces of the pyramidal holder 530 to a measurement target. The two optical detectors may also be obliquely disposed on the two side surfaces opposite to each other.

Also, optical irradiation paths and optical detection paths may be allowed to be formed such that the light sources and the optical detectors can irradiate light on the same region of the measurement target and detect light generated from the same region. Preferably, light sources and the optical detectors opposite to each other may be obliquely disposed at an angle of about 45 degrees with respect to the bottom surface of the pyramidal holder 530 adjacent to the measurement target, thereby significantly reducing an influence of the specular reflection.

Also, a pair of polarizers 515 and 516 and cross polarizers 517 and 518 may be disposed in the through-holes 531, 532, 533 and 534 together with optical filters 519 and 520 to minimize the influence of the specular reflection.

That is, the pyramidal holder 530 may be provided with a stepped part inside of the through-hole so as to store optical component such as polarizer, cross polarizer, and optical filter.

The polarizers 515 and 516, the cross polarizers 517 and 518, and the optical filters 519 and 520 may be disposed in the through-holes 531, 532, 533 and 534 so as to be adjacent to the bottom surface of the pyramidal holder 530 at the inner side of the light sources and the optical detectors.

The through-holes 531, 532, 533 and 534 formed in the four side surfaces of the pyramidal holder 530 may communicate with the center, and may be connected to the opening (535) of the bottom surface of the pyramidal holder 530.

A window 525 may be formed in the opening 535 to contact the measurement target, and the window 525 may be selected in consideration of the refractive index of light, and may be formed of a transparent material such as glass.

The window 525 may serve to protect surfaces contacting the skin and the sensor from foreign substances such as external humidity.

Also, a bottom plate 526 may be coupled to the bottom surface of the pyramidal holder 530 via a coupling member such as a bolt 527 to fix the window 525. The bottom plate 526 may have an opening at the center thereof such that the window 525 can be disposed.

Although not shown, the reflection detection type measurement apparatus for skin fluorescence may further include an optical connector that reduces a specular reflection component reflected from the skin surface that is a measurement target and allows light to effectively penetrate into the skin.

The optical connector may be configured to locate between the skin surface and the window 525 adjacent to the skin that is the measurement target and contact the window 525 and the skin surface, respectively.

Preferably, a step may be formed between the bottom of the bottom plate 526 and the undersurface of the window 525. The optical connector may be filled in the portion where the step is formed to form a structure in which the optical connector is contactable with the measurement target.

Accordingly, the optical connector may contact the window 525 and the surface of the skin to serve as a connection layer for enabling a smooth optical contact with an appropriate refractive index at the boundaries thereof. The optical connector may prevent the specular reflection from the surface of the skin, and may allow light to effectively penetrate into the skin.

The optical connector may have a certain refractive index between two media to prevent a light leakage that may occur between two media due to the refraction and scattering of the excitation light between the window 525 and the skin tissue, and may serve to fill uneven portions such as fine unevenness of the skin tissue.

The optical connector may be formed of an elastic material or a liquid material such as water or oil-immersion. Also, the optical connector may be formed of a material having a refractive index similar to those of the window 525 and the skin.

Meanwhile, mounting grooves may be formed in the through-holes 531, 532, 533 and 534 of the pyramidal holder 530 such that the light sources, the optical detectors, the polarizers, the cross polarizers, and the optical filters can be seated in the appropriate positions, respectively.

In FIG. 13, four side plates 521, 522, 523 and 524 may be fixedly mounted on the side surfaces of the pyramidal holder 530, and the light sources and the optical detectors may be mounted on the side plates 521, 522, 523 and 524. That is, the two light sources may be mounted at the inner side of the two side plates among the four side plates 521, 522, 523 and 524, and the two optical detectors may be mounted at the inner side of the other two side plates. The side plates 521, 522, 523 and 524 may be fixed on the pyramidal holder 530 by a coupling member such as the bolt 527.

Similarly to that described above, in FIG. 13, the optical irradiation from the light source to the measurement target and the optical detection of a fluorescence signal may be performed through the four through-holes 531, 532, 533 and 534.

The side views when viewed from the arrows "A" and "B" of FIG. 13 are shown in FIGS. 14 and 15. In FIGS. 14 and 15, the arrangement of the light sources, the optical detectors, the polarizers, and the optical filters are shown.

Hereinafter, an exemplary embodiment of the optical radiation, the optical detection, and the operation process performed by the reflection detection type measurement apparatus for skin fluorescence will be described as follows.

Example 3

It is necessary to perform measurement on a measurement target and a reference sample, two targets that are introduced to obtain a corrected fluorescence value. Light measurement is performed on the human body's skin that is the measurement target.

For diagnosis, the measurement is performed by a light source and an optical detector that contact or get close to the measurement target on the upper arm of a subject. A measurement scanner moves and scans along the skin surface to scan the target area of about 5 cm$^2$ to about 19 cm$^2$. The optical irradiation area of the reflection detection type pyramidal measurement apparatus for skin fluorescence may be about 15 mm in diameter at a time.

Before the measurement, all light sources are turned off, and then level evaluation of a dark signal is performed to automatically compensate for light leaking from the outside.

A light module sequentially generates first light source illumination light $\varphi(\lambda 1, t1)$ with a wavelength $\lambda 1$ and second light source illumination light $\varphi(\lambda 2, t2)$ with a wavelength $\lambda 2$ at different time intervals t1 and t2, respectively.

During the whole measurement process, light generated by two light sources is sequentially radiated at time intervals t1 and t2 while switching on/off is being repeated at a period of about 50 Hz.

Next, light irradiated from the light sources is detected by the optical detectors to be converted into electrical signals.

The first light source illumination light $\varphi(\lambda 1, t1)$ of a near-ultraviolet spectrum range (near 370 nm) excites the fluorescence of a target to form a corresponding signal $I(\lambda 2, t1)$ by the optical detector, and forms a signal $I(\lambda 1, t1)$ proportional to excitation reflected light diffuse-reflected by the skin that is the measurement target. For the test, the first optical detector 513 for measuring a reflected light single value of the target skin tissue in the excitation light wavelength used a 370 nm±20 nm UV bandpass filter as the optical filter 519, and a product #48-630 from Edmund Optics Inc was used.

The second light source illumination light $\varphi(\lambda 2, t2)$ of a blue spectrum range (near 440 nm) corresponds to the maximum value of the inherent fluorescence generated in AGE and NADH, and forms a signal $I(\lambda 2, t2)$ proportional to the emission light that is diffuse-reflected by the target skin. The second optical detector 514 for measuring an inherent fluorescence signal value of the skin tissue used a 440 nm±20 bandpass filter as the optical filter 520, and a product #86-340 from Edmund Optics Inc was used. In the second optical detector 514, a bandpass filter 520 as described above was used to transmit the inherent fluorescence of the skin tissue and interrupt the wavelength of the excitation light, i.e., about 370 nm reflected from the skin tissue.

The above measurement is repeatedly and periodically performed at different time intervals t1 and t2, and the measurement results are averaged and stored.

The same measurement processes are performed on the reference sample, and data calculated in each process is processed in an operation part to calculate a corrected skin fluorescence value.

Meanwhile, in order to obtain the corrected fluorescence signal value of the skin tissue, reflected lights reflected by the measurement target from the first light source 511 and the second light source 512 emitting light having a fluorescence wavelength have to be detected. However, since the intensity of the reflected light is relatively larger than the intensity of the inherent fluorescence emitted from the skin tissue, measurement signal saturation may occur in the first and second optical detectors upon detection of the reflected lights. Accordingly, in order for the optical detectors to simultaneously detect the reflected lights and the inherent fluorescence value without a loss, optical attenuation filters that reduce the amount of light within an irradiation range and do not generate fluorescence in a visible light range may be disposed on a portion of optical paths.

Figure 16:
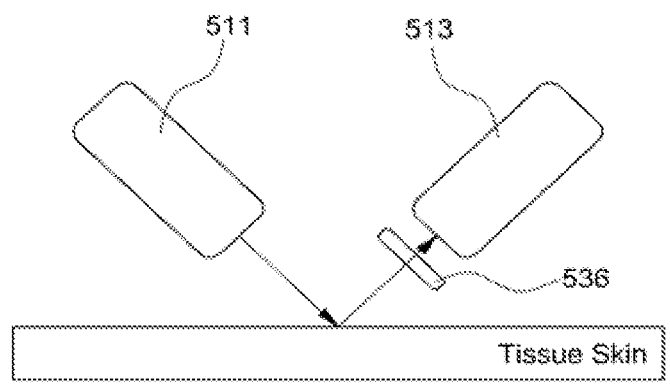
FIG. 16 is a view illustrating an optical attenuation filter in a reflection detection pyramidal measurement apparatus for skin fluorescence according to an embodiment of the present invention.
Figure 16:
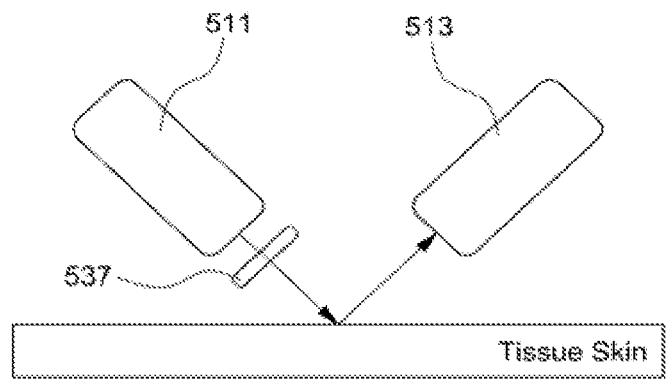

In this regard, FIG. 16 illustrates optical attenuation filters disposed at the front of the second light source and the first optical detector. In this embodiment, optical attenuation filters 536 and 537 may be disposed at the front of the second light source 512 and the first optical detector 513, and the optical attenuation filter may not be disposed at the first light source 511 and the second optical detector 514. That is, as shown in FIG. 16A, the optical attenuation filter 536 may be disposed at the front of the first optical detector 513, and as shown in FIG. 16B, the other optical attenuation filter 537 may be disposed at the front of the second light source.

Thus, the optical attenuation filters 536 and 537 can prevent saturation of the signal output in the first and second optical detectors 513 and 514 by lowering the intensity of the reflected light of the excitation light and the emission light. On the other hand, since the optical attenuation filter is not disposed at the front of the first light source 511 that excites the inherent fluorescence and the second optical detector 514 that detects the fluorescence signal, the fluorescence signal value can be detected without a loss.

As described above, a reflection detection type measurement apparatus for skin fluorescence according to an embodiment of the present invention has the following advantages.

First, in an embodiment of the present invention, since diabetic diseases can be easily diagnosed by evaluating the skin autofluorescence, mass inspection can be performed to find potential diabetic patients. In addition, the risk of cardiac-vascular diseases and complications thereof can be predicted.

Second, in an embodiment of the present invention, since the optical concentration and the optical uniformity of light irradiated from a light source are improved, more uniform light can be irradiated on the measurement target.

Third, in an embodiment of the present invention, since the optical efficiency can be improved by efficiently concentrating light from a light source on the skin tissue and minimizing the specular reflection on the surface of the skin tissue, the miniaturization of the apparatus can be achieved.

Fourth, in an embodiment of the present invention, since an error due to specular reflection generated on the skin surface and an error due to light scattering and absorption generated inside the skin can be corrected in measuring skin fluorescence, exact measurement of the skin fluorescence and exact diagnosis of diseases using the skin fluorescence can be achieved.

Fifth, in an embodiment of the present invention, the reflection detection type measurement apparatus for skin fluorescence may include light sources and optical detectors, and may be manufactured in a form of hand-grippable small-size scanner to measure the skin fluorescence. Thus, since a user can scan a diagnostic target by contacting the scanner with the skin of a subject, non-invasive diagnosis can be performed in real-time.

Sixth, in an embodiment of the present invention, since a selective diagnosis is enabled on certain body parts, and the area of the measurement target can be extended to a certain extent through the scanning method, the reliability of a signal and the accuracy of diagnosis can be improved.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A reflection detection type measurement method for skin fluorescence, the method comprising:
    irradiating excitation light on a measurement target;
    detecting a first reflected light and a skin fluorescence generated from the measurement target due to the excitation light;
    irradiating light with a same wavelength range of the skin fluorescence, which is generated from the measurement target due to the excitation light, on the measurement target;
    detecting a second reflected light generated from the measurement target due to the light with a wavelength range of the skin fluorescence; and
    calculating a skin fluorescence value of the measurement target by correcting a calculation based on the detected first reflected light, second reflected light and skin fluorescence.

2. The reflection detection type measurement method of claim 1, wherein a dark time is maintained for a certain time before irradiating the excitation light on the measurement target, and a dark signal value of the measurement target compensates the skin fluorescence value during the dark time.

3. The reflection detection type measurement method of claim 1, wherein a wavelength of the excitation light has a range of 370±20 nm.

4. The reflection detection type measurement method of claim 1, wherein a wavelength of the skin fluorescence has a range of 440±20 nm.

5. The reflection detection type measurement method of claim 1, wherein the excitation light and the skin fluorescence are irradiated on the same area of the measurement target.

6. The reflection detection type measurement method of claim 1, wherein the excitation light is irradiated on the measurement target for a first time, and the skin fluorescence is irradiated on the measurement target for a second time after the first time.

7. The reflection detection type measurement method of claim 1, wherein detecting the first reflected light and the skin fluorescence generated from the measurement target due to the excitation light comprises detecting light with a specific wavelength range of the first reflected light and the skin fluorescence.

8. The reflection detection type measurement method of claim 7, wherein a wavelength range of the reflected light is smaller than a wavelength range of the skin fluorescence.

9. A reflection detection type measurement apparatus for skin fluorescence, the apparatus comprising:
    a first light source irradiating light with a first wavelength range on a measurement target;
    a second light source irradiating light with a second wavelength range on the measurement target;
    a first optical detector detecting the light with a first wavelength range generated from the measurement target by the light of the first light source;
    a second optical detector detecting a skin fluorescence with the second wavelength range generated from the measurement target by the light of the first light source, and detecting the light with a second wavelength range generated from the measurement target by the light of the second light source;

a light source switching controller controlling a turned on/off of the first light source and the second light source; and an operation part for calculating a corrected skin fluorescence by correcting from a signal based on the detected light with a first wavelength range, light with a second wavelength range and skin fluorescence, wherein the light with the second wavelength range has a same wavelength range of light which is generated from the measurement target by the light with the first wavelength range.

10. The reflection detection type measurement apparatus of claim 9, wherein the light with a second wavelength range is longer than the light with a first wavelength range.

11. The reflection detection type measurement apparatus of claim 9, wherein the light source switching controller turns off the first light source and the second light source so as to maintain a dark time for a certain time before irradiating the light of the first light source.

12. The reflection detection type measurement apparatus of claim 9, wherein the light source switching controller turns off the first light source and the second light source so as to maintain a dark time for a certain time before irradiating the light of the second light source.

13. The reflection detection type measurement apparatus of claim 9, wherein the first optical detector is turned off while the second optical detector detects the light generated from the measurement target due to the light with a second wavelength range.

14. The reflection detection type measurement apparatus of claim 11, wherein the first optical detector and the second optical detector are turned on during a dark time maintained for a certain time before irradiating the light of the first light source.

15. The reflection detection type measurement apparatus of claim 12, wherein the first optical detector and the second optical detector are turned on during a dark time maintained for a certain time before irradiating the light of the second light source.

16. The reflection detection type measurement apparatus of claim 9, wherein the first wavelength range has a range of 370±20 nm.

17. The reflection detection type measurement apparatus of claim 9, wherein the second wavelength range has a range of 440±20 nm.

* * * * *